United States Patent [19]

Saint-Leger et al.

[11] 4,438,205

[45] Mar. 20, 1984

[54] PROCESS FOR SAMPLING AND ANALYSIS BY THIN LAYER CHROMATOGRAPHY

[75] Inventors: Didier J. Saint-Leger, Paris; André Abrioux, Drancy, both of France

[73] Assignee: "L'Oreal", Paris, France

[21] Appl. No.: 397,861

[22] Filed: Jul. 13, 1982

[30] Foreign Application Priority Data

Jul. 30, 1981 [FR] France ............................ 81 14816

[51] Int. Cl.³ ...................... G01N 31/08; G01N 33/92
[52] U.S. Cl. .................................. 436/71; 73/61.1 C;
128/749; 210/198.3; 210/658; 422/70; 436/162;
436/178
[58] Field of Search ................. 436/162, 174, 178, 71;
422/70; 73/61.1 C; 210/198.3, 656, 658;
128/749

[56] References Cited

U.S. PATENT DOCUMENTS

| | | | |
|---|---|---|---|
| 3,714,035 | 1/1973 | Jones | 210/658 |
| 3,785,930 | 1/1974 | Ellis | 422/56 X |
| 3,915,856 | 10/1975 | Meyer | 210/658 |
| 3,963,421 | 6/1976 | Jones | 422/70 X |
| 4,158,626 | 6/1979 | Halpaap et al. | 210/658 |
| 4,377,641 | 3/1983 | Dee et al. | 436/162 X |

Primary Examiner—Arnold Turk
Assistant Examiner—Robert J. Hill, Jr.
Attorney, Agent, or Firm—Cushman, Darby & Cushman

[57] ABSTRACT

Sampling and analyzing at least one mixture of substances by slab chromatography or thin layer chromatography involves sampling the mixture on a non-adsorbent solid support using a sampling member to achieve precisely repeatable conditions, depositing an appropriate amount of the mixture to be analyzed on an edge zone of a chromatography plate, bringing the said edge of the chromatography plate into contact with a solvent or a mixture of solvents to cause the migration of the mixture on the chromatography plate and the separation of the constituents of the said mixture, and developing the said plate for the qualitative and/or quantitative analysis of the constituents of the mixture, by pressing that face of the support which bears the mixture against the chromatography plate until the mixture to be analyzed has essentially migrated entirely out of the abovementioned support.

The action of pressing the support against the chromatography plate is carried out with the aid of a specially designed holding means fastened to the chromatography plate.

7 Claims, 7 Drawing Figures

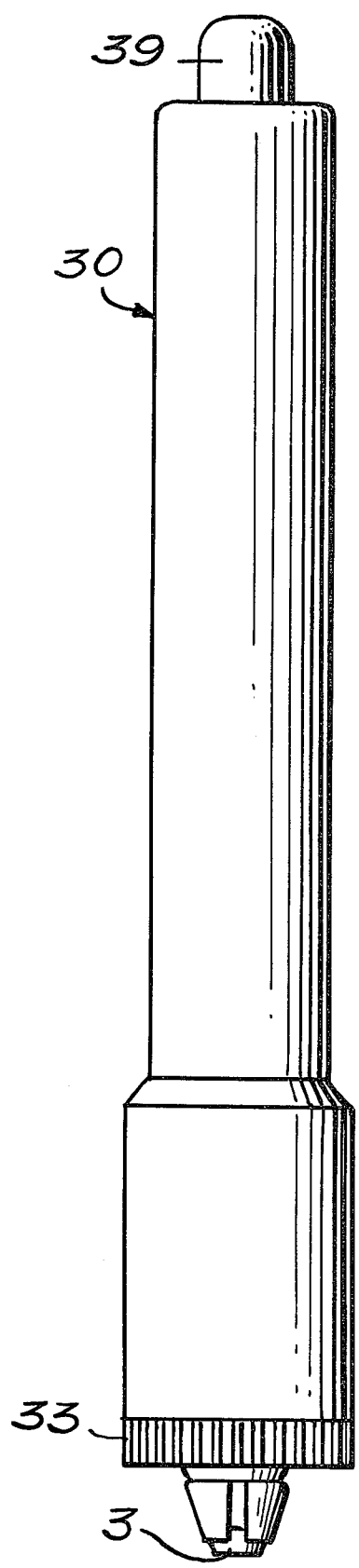
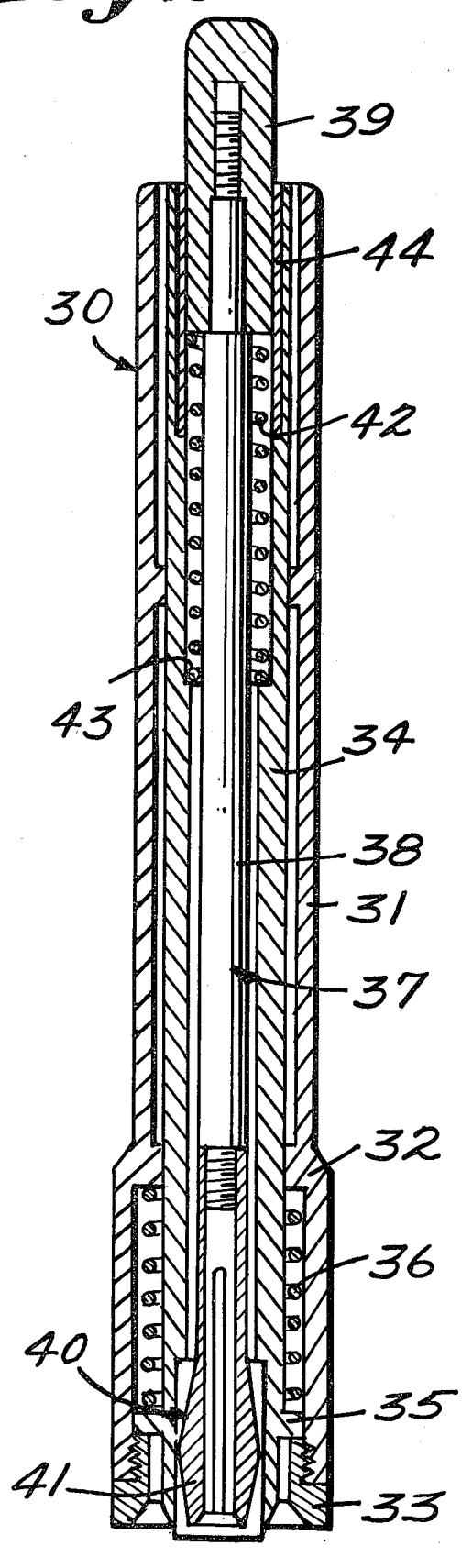

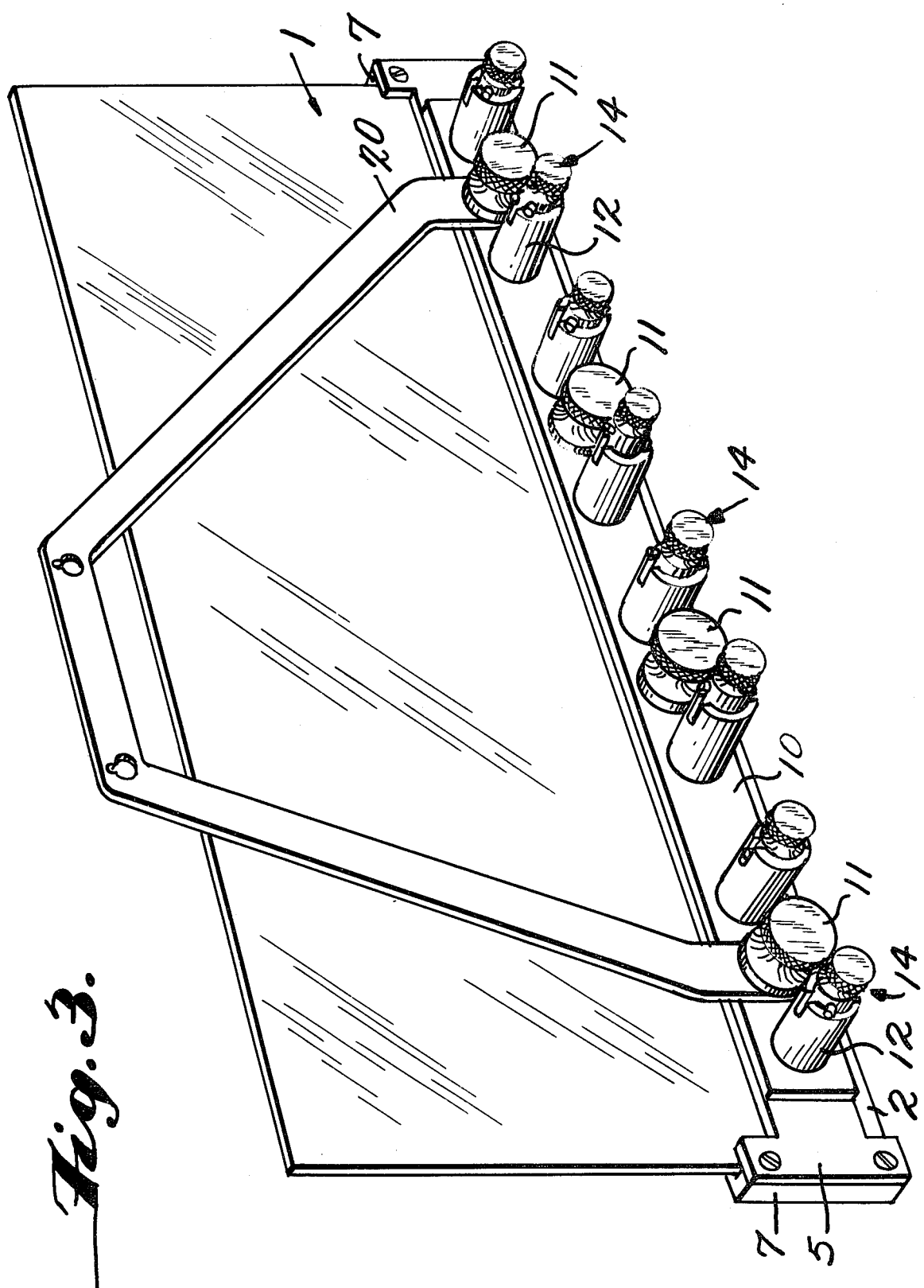

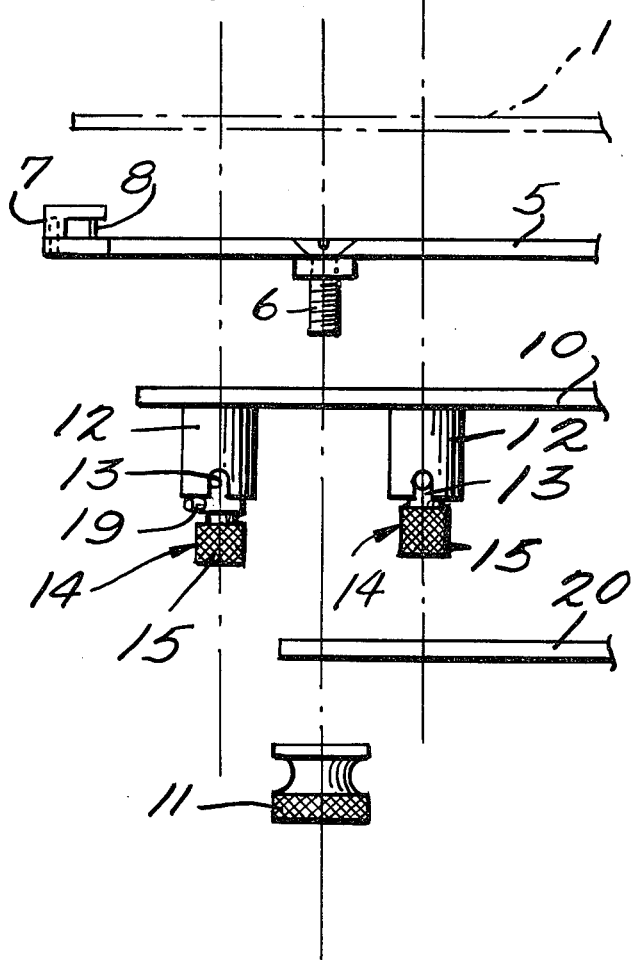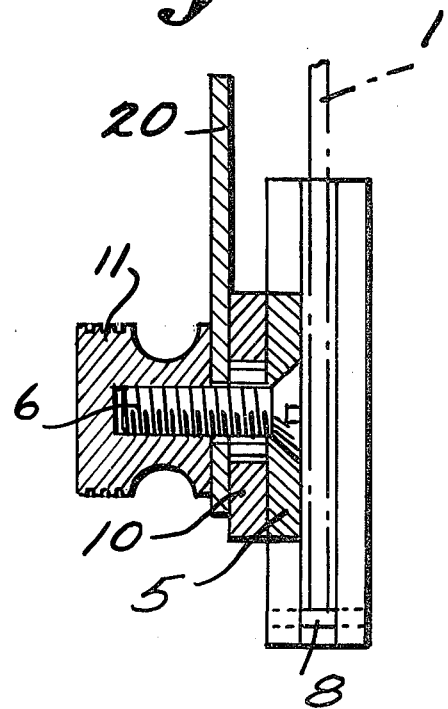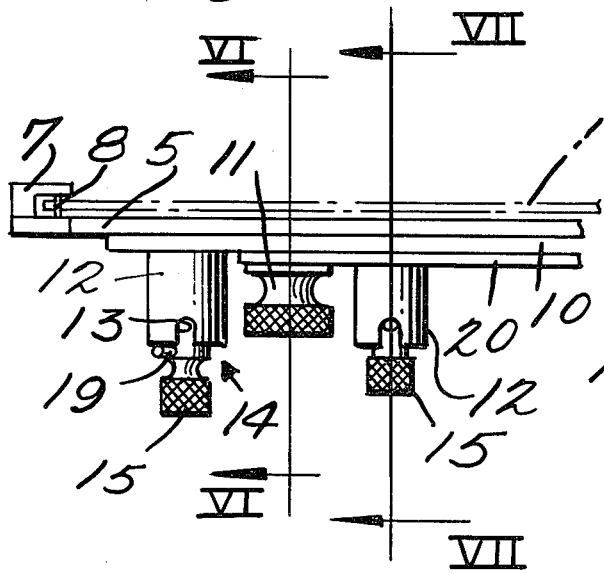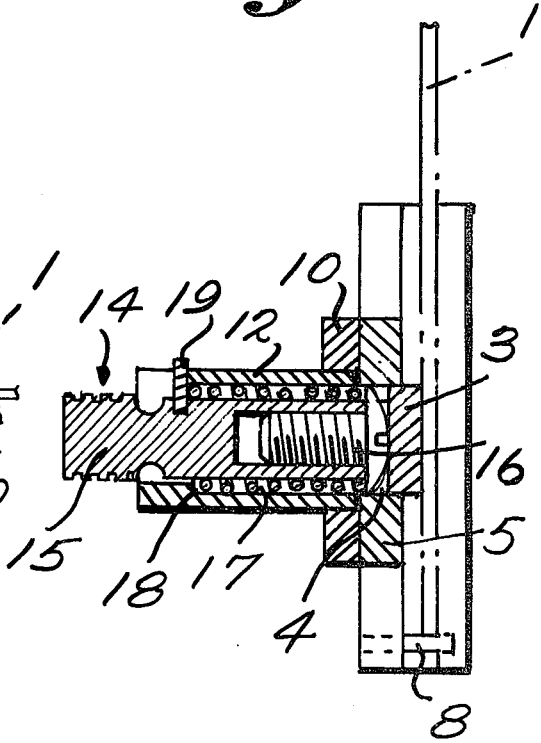

PROCESS FOR SAMPLING AND ANALYSIS BY THIN LAYER CHROMATOGRAPHY

BACKGROUND OF THE INVENTION

The present invention relates to a process for sampling and analyzing at least one mixture of substances by slab chromatography or thin layer chromatography, which consists in depositing on the chromatography plate an appropriate amount of the mixture to be analyzed, in bringing the chromatography plate into contact with a solvent or a mixture of solvents so as to cause the migration of the mixture on the plate and the separation of the constituents of the said mixture, and in developing the said plate by means, for example chemical or physicochemical means, for the qualitative and/or quantitative analysis of the constituents of the mixture.

The abovementioned method is well known and widely used in the laboratory. Slab chromatography or thin layer chromatography generally uses a glass plate on which a thin layer, having a thickness of 100 to 300 microns, of an absorbent substance such as, for example, silica is deposited. A drop of the mixture to be examined is deposited on this chromatography plate; it is then left to dry; the chromatography plate is then placed inside a tank, for example virtually, with its base dipping in a trough containing a solvent or a mixture of solvents, which rises up the plate by capillary action. The various constituents of the mixture to be analyzed will migrate to a greater or lesser extent along a vertical line and produce spots which will then be developed. The position of the spots makes it possible to determine the nature of each of the constituents.

The mixture to be subjected to analysis may be present on a substrate. This is the case, for example, with the sebum secreted by the skin, and it is desirable, in dermatology, to know the nature of the sebum and the relative proportions of the lipids of which it is composed. The mixture to be analyzed can be removed from the substrate by means of a solvent. It can also be removed more conveniently by means of a plane support, such as a small glass square. However, in the latter case, it is nevertheless necessary to use a solvent in order to transfer the sample removed by the plane support into the said solvent, by dilution. The volume of solvent used must be large if it is desired to recover all the sample, which is essential if it is desired to determine the relative proportions of the constituents of the mixture. Thus, a solution is obtained which has an extremely low concentration of solute, and it is consequently necessary to concentrate it before depositing it on the chromatography plate. All these dilution and concentration steps complicate the chromatographic analysis and prove expensive in terms of time and skilled personnel.

Another disadvantage of analysis by thin layer chromatography is the small size of the samples subjected to analysis, which are generally between 1 and 5 microliters and may at the extreme limit be as much as 20 microliters. In fact, the chromatographic separation of the constituents of a mixture is all the more successful, the smaller the amount of mixture to be analyzed; however, this small size of the samples is a source of difficulty if it is desired to carry out a precise quantitative analysis of the constituents of the mixture.

Plates have recently been marketed which possess a layer of diatomaceous earth as the concentration zone, where the samples are deposited. These plates make it possible to deposit a larger amount of sample, which can be as much as about 500 microliters, without detracting from the quality of the separation. Nevertheless, chromatography plates of this type, like the conventional chromatography plates, requires a step for dilution, with a solvent, of the sample removed by a plane support, followed by a step for concentration of the solution obtained.

SUMMARY OF THE INVENTION

The object of the present invention is to overcome the abovementioned disadvantage. According to the present invention, in a process for sampling and analysis by thin layer chromatography the abovementioned steps of dilution and concentration are dispensed with and the mixture to be analyzed is instead removed, in a conventional manner, from the substrate on which it is present by means of a non-adsorbent plane support, such as a thin plate or disc of frosted glass. Instead of being diluted in a large volume of solvent, as in the conventional method, the sample removed by the plane support is applied directly to the chromatography plate without any other subsequent treatment, the plane support being applied and fixed to the chromatography plate for the time required for the sample to migrate entirely out of the plane support.

The present invention also relates to a device specially designed for keeping the support on which the mixture to be analyzed is deposited pressed against the chromatography plate and also relates to a member specially designed for taking samples from a substrate under reproducible conditions, that is to say with an application pressure of the support on the substrate which is virtually unchanged from one sampling to the next.

The present invention therefore relates to a process for sampling and analysis by slab chromatography or thin layer chromatography of the type defined above which process comprises depositing, on an edge zone of the chromatography plate, the mixture to be analyzed which has been removed by a non-absorbent support, the said support being pressed directly, with its face on which the mixture to be analyzed is present, against the said edge zone of the chromatography plate, and the said support being kept pressed against the chromatography plate essentially until the mixture to be analyzed has migrated entirely out of the abovementioned support.

In order to check whether the mixture to be analyzed has migrated entirely out of its support, it is possible, in particular, to apply the support to a new chromatography plate and to observe whether other substances are capable of migrating out of the said support.

The support used is preferably a non-adsorbent rigid body and in particular a small plane support, such as a thin plate or a disc. The plane support is advantageously made of glass and, of its two faces, the one on which the mixture to be analyzed is deposited is frosted.

In a preferred embodiment, the mixture to be analyzed is removed from the solid substrate on which it is present by means of a non-adsorbent support under reproducible conditions, and, to do this, the abovementioned support is applied to the substrate under a predetermined pressure and for a predetermined time.

In general, any type of chromatography plate can be used in the process according to the invention. However, it is preferred to use those possessing a concentration zone in which are to be deposited the mixtures to be analyzed and the reference mixtures for comparison, this concentration zone consisting of a thin layer of diatomaceous earth placed alongside the thin layer of absorbent substance, which preferably consists of silica.

According to another advantageous characteristic of the process according to the invention, the support to which the mixture to be analyzed has been applied is held against the chromatography plate by elastic means, such as, for example, a push-rod pushed by a spring against the chromatography plate.

Preferably, not only the support by which the mixture to be analyzed has been removed but also other supports on which standard reference substances or mixtures are deposited are applied to the same chromatography plate, the standard mixtures being chosen so as to have characteristics similar to those of the mixture to be analyzed.

Once the mixture to be studied and the reference substances or mixtures have been applied to the chromatography plate by means of non-adsorbent supports, the chromatographic analysis is performed in a conventional manner. The process according to the invention applies both to partition chromatography and to adsorption chromatography. In a known manner the migrating solvents, pure or as a mixture, are appropriately chosen, for example so as to vary the polarity or the pH of the medium according to the mixture of substances to be separated.

The process according to the invention can be used very particularly in dermatology for the qualitative and quantitative determination of the sebum secreted by the skin. In this case, the substrate from which the sample is removed consists of the skin "in vivo". However, it can of course be used in other applications without thereby exceeding the scope of the invention.

The present invention also relates to a device designed for carrying out the process defined above for keeping the support on which has been deposited the mixture to be analyzed and, if appropriate, other supports on which the standard substances or mixtures have been deposited, pressed against the chromatography plate. This device possesses, firstly, at least one housing open at both ends, in which is placed the support of the mixture to be analyzed, the wall of the said housing being opposite a chromatography plate, and secondly means which on the one hand are arranged at that end of the housing opposite the chromatography plate, and on the other hand are detachably fastened to the wall in which the abovementioned housing is made, in order elastically to press the support located inside the housing against the chromatography plate.

Preferably, in particular in the case where the chromatography plate is intended to be placed vertically inside the chromatography tank, the housing in which the support of the mixture to be analyzed is located consists of a bore made in a support plate terminating at both ends in corner pieces, where the chromatography plate is positioned and supported.

The means for elastically pressing the support for the mixture to be studied against the chromatography plate inside the housing in the support plate, advantageously consist of a counter-plate screwed to the support plate, a push-rod subjected to the action of at least one spring, passing through the said counter-plate at the location of the abovementioned housing, the said push-rod being capable of adopting two positions, namely a position in which it projects into the housing and a retracted position in which it does not project into the said housing.

The support plate advantageously possesses a plurality of uniformly spaced housings extending along its longitudinal axis; in this case, the counter-plate possesses an equal number of push-rods, each push-rod being guided inside a sleeve projecting from that longitudinal face of the counter-plate which does not press on the support plate. Preferably, the chromatography plate is suspended inside the tank by means of a detachable holder screwed to the support plate and its associated counterplate.

Finally the present invention relates to a manual sampling member making it possible to pick up a non-adsorbent support intended for receiving the mixture to be analyzed, to apply it to a substrate under a predetermined pressure provided by at least one calibrated spring, and to release the support in a housing in the device defined above once the sampling has been carried out. A sampling member of this type comprises, inside a rigid body of elongate cylindrical shape which is open at both ends, a sheath displaceable axially inside the rigid body against the action of at least one calibrated spring threaded around the said sheath. An element for gripping the support intended for receiving the mixture to be studied or the standard substances or mixtures is advantageously fitted inside the sheath, the said element being axially displaceable inside the said sheath against the action of a return spring threaded around the said element. The gripping element advantageously comprises a rod, at one end of which is fastened a push-rod projecting outside thwe body of the member; at its other end, the abovementioned rod is provided with a clamp consisting of elastic strips separated by axial slots, the said strips being brought radially closer together in the sheath in which they are located, when the push-rod is not subjected to any pushing action.

BRIEF DESCRIPTION OF THE DRAWINGS

Other advantages and characteristics of the invention will become apparent on reading the description which follows, which is given by way of a non-limiting example and refers to the attached drawing.

In this drawing:

FIG. 1 is a view in elevation of the sampling member according to the invention, the support to which the mixture to be analyzed is to be applied being housed inside the clamp of the said member;

FIG. 2 is an axial section of the sampling member of FIG. 1, in the rest position;

FIG. 3 is a view in perspective showing a chromatography plate and a device, according to the invention, designed for keeping the support to which the mixture to be analyzed is to be applied pressed against the plate;

FIG. 4 is a partial exploded view of the various elements constituting the device of FIG. 3;

FIG. 5 is a partial section along V—V of FIG. 3;

FIG. 6 is a section along VI—VI of FIG. 5; and

FIG. 7 is a section along VII—VII of FIG. 5.

DESCRIPTION OF THE PREFERRED EMBODIMENT

In FIG. 3, 1 denotes a chromatography plate marketed under the name "Whatman LHPK". It is intended to be suspended vertically inside a tank with its base arranged in a conventional manner inside a trough containing a solvent or a mixture of solvents. It consists of a glass plate coated with a thin layer of silica having a thickness of about 250 microns, which extends over a height of about 10 cm. At its base, over a height of about 2 cm, it possesses a concentration zone 2 consisting of a thin layer of diatomaceous earth. Droplets of the mixture to be analyzed, and of the appropriate standards, are usually deposited on the concentration zone 2. As is known, the layer of diatomaceous earth 2 makes it possible to deposit a larger amount of mixture, which can be as much as 500 microliters, while permitting a good separation, whereas for a conventional chromatography plate the amount of samples cannot exceed 20 microliters and is generally between 1 and 5 microliters.

In this example the sample to be analyzed and the standards are applied to non-adsorbent plane supports consisting of discs 3 of frosted glass (FIGS. 1 and 7) having a diameter of about 6 mm.

The sample to be analyzed and the standards are deposited on the frosted face of the discs 3 and are removed by means of a member which will be described in detail below in connection with FIGS. 1 and 2.

After sampling, the glass discs 3 are arranged inside cylindrical housings 4 made in a support plate 5. In this example, eight housings 4 are provided, which are all identical and pass right through the support plate 5. The housings 4 are uniformly spaced and arranged along the longitudinal axis of the support plate 5.

The support plate 5 is made of stainless steel. It is fixed by four connecting screws 6 (FIGS. 4 and 6) with countersunk heads, the threaded stems of which project from the front face of the support plate 5, that is to say from the face which is opposite the chromatography plate 1. At its ends, the support plate 5 is provided, on its rear face, with two corner pieces 7 facing one another. The two corner pieces 7 are riveted to the support plate 5. The chromatography plate 1 is loosely mounted between the two corner pieces 7 and the support plate 5; it bears on two stop pins 8, which are supported at their ends by the support plate 5 on the one hand, and by the parallel flange of the corresponding corner piece 7 on the other hand.

Two small studs (not shown) project from the rear face of the support plate 5 in line with the two corner pieces 7, but keep the chromatography plate 1 away from the support plate 5; this separation is approximately 1 mm and is less than the thickness of one glass disc 3. The housings 4 in the glass discs 3 are located essentially along the longitudinal median axis of the concentration zone 2 of the chromatography plate 1.

A counter-plate 10, also made of stainless steel, can be clamped against the front face of the support plate 5 by means of four milled nuts 11 cooperating with the connecting screws 6 of the support plate 5. The width of the counter-plate 10 is essentially equal to that of the support plate 5, but its length is slightly less. At the location of each housing 4 in the support plate 5, the counter-plate 10 possesses a hole in which a cylindrical sleeve 12 is crimped. The counter-plate 10 is therefore fixed to eight uniformly spaced sleeves 12, the axes of which are perpendicular to the plane of the plate; the sleeves 12 only project from the front face of the counter-plate 10, so that the latter can be applied flat against the support plate 5. Two diametrically opposite notches 13 are made in the free edges of the sleeves 12 which are opposite the counter-plate 10.

A push-rod 14, possessing a milled head 15, is slidably mounted inside the sleeves 12. A threaded axial hole, into which a round-headed screw 16 is inserted, is made in that end of the push-rod 14 which is opposite the milled head 15. The head of the screw 16, which projects radially relative to the body of the push-rod 14, constitutes one of the two stops for a helical spring 17 threaded around the push-rod 15 inside the sleeve 12. The other stop for the helical spring 17 consists of a shoulder 18 made on the inner wall of the sleeve 12. The spring 17 tends to displace the push-rod 15 in the direction of the chromatography plate 1, so that the round head of the screw 16 projects into the housings 4 in the plate 5.

The push-rod 14 is fixed to a stop pin 19, which enables it to adopt two positions: a retracted position in which the pin 19 is pressed against the peripheral rim of the sleeve 12, and an extended position in which the stop pin 19 bears against the bottom of one of the two diametrically opposite grooves 13, the changeover from one of the two positions to the other being effected by rotating the push-rod 14 inside the sleeve 12 by at most a quarter of a turn.

The assembly formed by the support plate 5, the counter-plate 10 screwed to the support plate 5, and the chromatography plate 1 is suspended inside a chromatography tank of known type, by means of a U-shaped stainless steel holder 20 which is screwed by means of two milled nuts 11 to connecting screws 6 of the support plate 5.

FIGS. 1 and 2 show the member for removing a mixture to be analyzed from a substrate, such as, for example, skin "in vivo", by means of a disc of frosted glass 3. A member of this type has been designated by 30 in its entirety. Its purpose is:

to pick up a disc of ground glass 3 with which it is desired to remove a sample;

to apply the disc of ground glass 3 to the substrate under a predetermined pressure; and once the sample has been removed, to release the ground glass disc 3 at the location of a housing 4 in the support plate 5, in order to introduce it into the said housing.

The sampling member 30 is provided with a rigid body 31 of elongate cylindrical shape, which is open at both ends; the body 31 comprises two sections of different internal diameters, joined by a shoulder 32. A tip 33 is screwed to the free end of the section of larger diameter, which faces the substrate.

A sheath 34, which is also open at both ends, is slidably mounted inside the body 31 of the sampling member. It is provided with a peripheral collar 35 pushed against the tip 33 by means of a calibrated helical spring 36, which is threaded inside the body 31, around the sheath 34, and which bears against the internal shoulder 32. A Teflon ring 44 is crimped inside the sheath 34, in the region of its end opposite the tip 33.

A gripping element 37 is slidably mounted inside the sheath 34: it comprises a rod 38, to one end of which is screwed a push-rod 39 which emerges perpendicularly at the end of the body 31 opposite the tip 33. A clamp 40, comprising three elastic strips 41 of curved cross-section, separated by axial slots, is screwed to the other end of the rod 38.

The push-rod 39 serves as a stop for a return spring 42, which is threaded around the rod 38 and which presses on a shoulder 43 made on the internal wall of the sheath 34.

The operation of the sampling member 30 is comparable to that of an ever-sharp propelling pencil of conventional type, equipped with an additional calibrated spring. To pick up a disc of frosted glass 3, the operator grips the body 31 of the sampling member in the palm of his hand and presses on the push-rod 39, for example with his thumb. He thus causes the displacement of the rod 38 and of its adjoining clamp 40 inside the sheath 34, this movement being performed against the action of the return spring 42. The clamp 40 can then project out of the tip 33, and its three strips 41, which were forced radially inwards by the sheath 34, can move apart. The opertor places the ground glass disc 3 inside the circular passage defined by the three separated strips 41 of the emerging clamp 40. As soon as the operator relaxes the pressure, the clamp 40 is pushed back into the sheath 34; the three elastic strips 41 are therefore moved radially inwards and consequently grip the ground glass disc 3.

To apply the ground glass disc 3, held by the clamp 40 of the sampling member, to the substrate, the operator holds the member by its body 31 and pushes it against the substrate so as to displace the body 31 axially relative to the sheath 34, against the action of the calibrated spring 36, and thus to bring the tip 33 essentially into contact with the substrate. The calibration of the spring 36 is chosen so as to apply an essentially constant pressure to the substrate, whether the spring 36 is compressed to a small or a large extent. For a predetermined constant period of time, the operator keeps the ground glass disc 3 applied against the substrate.

After sampling, the pressing of the ground glass disc 3 on a chromatography plate 1, by means of the devices of FIGS. 3 to 7, is carried out as follows: With the counter-plate 10 not fixed to the support plate 5 the chromatography plate 1 is introduced between the two corner pieces 7 thereof, and this assembly is then laid essentially flat, for example on a bench, with the support plate 5 superposed on the chromatography plate 1. The sampling member 30 is brought in line with one of the housings 4 in the support plate 5, and, by acting on the push-rod 39, the operator releases the ground glass disc 3 and drops it into the chosen housing 4 against the chromatography plate 1. By repeating the operation chosen above, the operator can fill each of the housings 4 with ground glass discs 3 on which have been deposited other samples to be studied, or suitably chosen standards.

When this operation is complete, the counter-plate 10, with all the push-rods 14 in the retracted position, is applied to the support plate 5, followed by the holder 20, these two elements being placed over the connecting screws 6 of the support plate 5, and the whole is fixed by means of the milled nuts 11; finally, the push-rods 14 are rotated in order to change them over to their extended position.

The device of FIGS. 3 to 7 and the sampling member 30 of FIGS. 1 and 2 can be used in particular in dermatology for analyzing sebum. In this case, a ground glass disc 3 is applied to the skin (forehead or scalp) by means of the sampling member 30, for a period of about 15 seconds; this period is chosen so as to remove a sample which is neither too small nor too large. Without any subsequent treatment, the ground glass disc 3 is placed in position against the concentration zone 2 of the chromatography plate 1, as described above, by means of the device of FIGS. 3 to 7. Care is taken to place standard mixtures on either side of the sample, these mixtures also having been deposited on ground glass discs 3. These standard mixtures are appropriately chosen so as to have characteristics similar to those of the mixture of lipids to be studied. The assembly shown in FIG. 3 is then suspended inside a chromatography tank of conventional type with the base of the concentration zone 2 dipped in a solvent, the solvent level of course being below the ground glass discs 3.

Elution is carried out in the conventional way: the migration solvent passes over the diatomaceous earth and then over the silica of the plate 1. When the ground glass disc 3 held by the device described above is in contact with the silica, the solvent elutes the mixture of lipids located on the said ground glass: the migration solvent also behaves like an elution solvent. The various lipids in the mixture are separated by means of the following three baths in succession: hexane, hexane/ether (90/10) and hexane/ether/acetic acid (70/30/1). It should be noted that the elution of the chromatography plate 1 is complete as from the second bath. Upon emergence from the second bath, the chromatography plate 1 can be separated from the support plate 5 and its adjoining counter-plate 10. The chromatography plate 1 is dried and then immersed in a 3% strength solution of sulfuric acid. The chromatography plate is then left in an oven for a period of about 30 minutes at a temperature of about 170° C.

At least five different spots then appear, which are very well separated. They correspond to the following constituents (classified in order of increasing $R_f$):

cholesterol
free fatty acids
triglycerides
monoester waxes
squalene.

Other spots, depending on the type of skin, may appear:

diglycerides (before the cholesterol)
diester waxes (between the triglycerides and the monoester waxes).

The quantitative analysis of each of the separated constituents is carried out by determining the intensity of the color of the spot (photodensitometry); by virtue of the presence of the standard mixtures placed on either side of the sample, the photodensitometer gives a linear response after calibration. It is therefore possible to know the exact amounts of each constitutent present in each sample. The precision is of the order of 0.5%.

This method proves to be particularly sensitive, since it makes it possible to detect amounts of constituent of as little as 0.2 $\mu$g (for example, cholesterol: 0.2 $\mu$g; waxes: 1 $\mu$g; squalene: 0.5 $\mu$g).

The greater analytical sensitivity which is obtained with the method described above, as compared with the conventional method, results mainly from the fact that the samples in the conventional method could not exceed 20 microliters, whereas, in the present method, they can be as much as 500 microliters, which obviously improves the quantitative analysis.

Another major advantage of the present method is that it is particularly simple and rapid, since the stages of dissolution of the samples and then of concentration of the solution obtained, before it is applied to the chromatography plate, are dispensed with. In the present invention, transfer is made directly from the substrate on which the mixture to be studied is present, using any non-adsorbent solid carrier to transfer the sample from the substrate to the chromatography plate, without any intermediate treatment, the carrier being fixed to the plate during the chromatography.

Because it dispenses with the difficult operations of dilution of the sample and of concentration of the solution obtained, the method according to the invention can be carried out even by persons who are not expert in laboratory techniques, and can be used without difficulty for routine checks.

Of course, the embodiment described above in no way implies a limitation and will be able to form the subject of any desirable modifications without thereby exceeding the scope of the invention.

We claim:

1. A process for sampling and analyzing at least one mixture of substances by thin layer chromatography, said process comprising the steps of:
   (a) sampling the said mixture by means of a non-adsorbent solid support;
   (b) depositing the thus sampled mixture on a chromatography plate by pressing the said non-adsorbent support, by its face which bears the mixture to be analyzed, directly against an edge zone of the said chromatography plate;
   (c) bringing the said edge of the chromatography plate into contact with a solvent or a mixture of solvents, so as to cause the migration of the mixture on the chromatography plate and the separation of the constituents of the said mixture; and
   (d) developing the said plate for at least one of the qualitative and quantitative analysis of the constituents of the mixture by keeping the said support pressed against the chromatography plate until the mixture to be analyzed has essentially migrated entirely out of the said support.

2. A process according to claim 1, wherein the non-adsorbent support used is a small, essentially rigid plane support.

3. A process according to claim 2, wherein the plane support is a piece of frosted glass.

4. A process according to any one of claims 1 to 3, wherein the mixture to be analyzed is removed from a solid substrate on which it is present, by applying the non-adsorbent solid support to the substrate under a predetermined pressure and for a predetermined time to obtain a desired sample size.

5. A process according to any one of claims 1 to 3, wherein the chromatography plate includes a thin layer of absorbent silica and alongside said thin layer, a concentration edge zone comprising a thin layer of diatomaceous earth for receiving said mixture to be analyzed.

6. A process according to any one of claims 1 to 3, wherein the non-adsorbent support on which the mixture to be analyzed has been deposited is held against the chromatography plate by elastic means.

7. A process according to any one of claims 1 to 3, wherein the mixture to be analyzed is sebum removed from the skin "in vivo".

* * * * *